United States Patent
Yoo et al.

(10) Patent No.: US 11,389,393 B2
(45) Date of Patent: Jul. 19, 2022

(54) COMPOSITION FOR INHIBITING SEBUM SECRETION COMPRISING PEACH SPROUT EXTRACT

(71) Applicant: AMOREPACIFIC CORPORATION, Seoul (KR)

(72) Inventors: Se Jin Yoo, Yongin-si (KR); Nok Hyun Park, Yongin-si (KR); Yu Jin Oh, Yongin-si (KR); Hyunwoo Lee, Yongin-si (KR); Yong-Jin Kim, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 663 days.

(21) Appl. No.: 16/321,782

(22) PCT Filed: Jul. 25, 2017

(86) PCT No.: PCT/KR2017/008004
§ 371 (c)(1),
(2) Date: Jan. 29, 2019

(87) PCT Pub. No.: WO2018/021802
PCT Pub. Date: Feb. 1, 2018

(65) Prior Publication Data
US 2021/0275435 A1  Sep. 9, 2021

(30) Foreign Application Priority Data
Jul. 29, 2016 (KR) .................. 10-2016-0097336

(51) Int. Cl.
*A61K 36/65* (2006.01)
*A61K 36/736* (2006.01)
*A61Q 19/00* (2006.01)
*A61K 8/9789* (2017.01)

(52) U.S. Cl.
CPC ............ *A61K 8/9789* (2017.08); *A61K 36/65* (2013.01); *A61K 36/736* (2013.01); *A61Q 19/008* (2013.01); *A61K 2236/331* (2013.01); *A61K 2800/805* (2013.01)

(58) Field of Classification Search
None
See application file for complete search history.

(56) References Cited

FOREIGN PATENT DOCUMENTS

| CN | 101965178 A | 2/2011 |
|---|---|---|
| CN | 103611025 A | 3/2014 |
| CN | 104042923 A | 9/2014 |
| CN | 105596281 A | 5/2016 |
| CN | 105726693 A | 7/2016 |
| CN | 105769707 A | 7/2016 |
| EP | 1219296 A4 | 12/2004 |
| JP | 2015-86183 A | 5/2015 |
| KR | 10-1998-0045931 A | 9/1998 |
| KR | 10-0286534 B1 | 1/2001 |
| KR | 1019980045931 * | 6/2005 |
| KR | 10-0756669 B1 | 9/2007 |
| KR | 10-2009-0035274 A | 4/2009 |
| KR | 10-0893912 B1 | 4/2009 |
| KR | 10-2009-0092235 A | 8/2009 |
| KR | 10-1473940 B1 | 12/2014 |
| KR | 10-2015-0032546 A | 3/2015 |

OTHER PUBLICATIONS

Hwang, Primera puts "Men Organience Sebum Cut Fluid" on the market, Busan.com Mar. 17, 2016, p. 1 Internet:URL:http://news20.busan.com/controller/newsController.jsp?newsId=20160316000291#none.*
Abstract, CN 1891284 (2007).*
International Search Report from International Application No. PCT/KR2017/008004, dated Nov. 6, 2017.
Written Opinion from International Application No. PCT/KR2017/008004, dated Nov. 6, 2017.
Hwang, Sang Uk, "Primera, Put "Men Orga.'lience Sebmn Cut Fluid" on the Market", Busan.com, Mar. 17, 2016, p. 1, Internet: <URL: http://news20.busan.com/controller/newsController.jsp?newsId=20160316000291#none>.
Hwang, Sang Uk, "Primera, Put "Men Orga.'lience Sebum Cut Fluid" on the Market", Busan.com, Mar. 16, 2016, p. 1, Internet: <URL: http://news20.busan.com/controller/newsController.jsp?newsId=20160316000291#none>.
Office Action for Korean Patent Application for 10-2016-0097336 (dated May 18, 2021).
Juju Ryu et al., "Use and Protection of Human Organs", People's Army Publishing House: 82-83 (2014) (see Brief English translation of the Chinese Office Action No. 201780056877.4 of Jun. 29, 2021).
Yao Xin-cheng et al., "Review on Natural Plants with 5α-Reductase Inhibitory Effect", Nat Prod Res Dev, vol. 26(5): 800-805 (2014).
Chen Jian-xin et al., "Study on Extraction of Flavonoids in Peach Leaves", Guangzhou Chemical Industry, vol. 44(7): 88-90 (2016).
Gulfishal et al., "Lipoxygenase assay and cutaneous erythema test have discovered a potent anti-inflammatory activity shown by some genus *Prunus* plants", Scientific Research and Essays, vol. 9(23): 988-992 (2014).
Office Action for Chinese Patent Application No. 201780056877.4 (dated Jun. 29, 2021).

\* cited by examiner

*Primary Examiner* — H. Sarah Park
(74) *Attorney, Agent, or Firm* — Merchant & Gould P.C.

(57) ABSTRACT

Disclosed herein are a composition for inhibiting sebum secretion comprising a peach sprout extract as an active ingredient, and a composition for inhibiting sebum secretion comprising a mixed extract of peach sprout and peony as an active ingredient. The extract can inhibit an overproduction of sebum and regulates secretion of sebum, thereby not only imparting elasticity to the pores but also suppressing the aging of the pores and exhibiting a pore-contraction effect.

9 Claims, 7 Drawing Sheets

Promotion of sebum secretion

Promotion of sebum secretion + peony extract 5 ppm

Promotion of sebum secretion + peony extract 10 ppm

COMPOSITION FOR INHIBITING SEBUM SECRETION COMPRISING PEACH SPROUT EXTRACT

This application is a National Stage Application of International Application No. PCT/KR2017/008004, filed 25 Jul. 2017, which claims benefit of Serial No. 10-2016-0097336, filed 29 Jul. 2016 in the Republic of Korea and which applications are incorporated herein by reference. To the extent appropriate, a claim of priority is made to each of the above disclosed applications.

TECHNICAL FIELD

Disclosed herein are a composition for inhibiting sebum secretion comprising a peach sprout extract as an active ingredient, and a composition for inhibiting sebum secretion comprising a mixed extract of peach sprout and peony as an active ingredient.

BACKGROUND ART

In general, sebum generated in the skin, including the scalp and the face, plays a role of retaining the moisture of the skin and preventing microbial invasion. However, excessive secretion of sebum may cause oily skin, cakey makeup, and enlargement and aging of the pores and may encourage the production of post-puberty acne.

Many causes are involved in sebum secretion. Among them, the activation of sebaceous gland cells by the action of hormones is known to be the most important cause.

Thus, previously, female hormones such as estrogen were used for the treatment of excessive secretion of sebum or acne caused by male hormones. However, currently, they are not used or used in a trace amount due to the skin inflammation, side effects caused by hormone administration, etc.

Currently used methods for inhibiting sebum secretion by using cosmetics include a method of using a porous powder that temporarily absorbs sebum or a method of using an extract known to inhibit sebum. However, they have an insignificant effect because the content of the active ingredient is very small.

Peach contains polyphenols, amygdalin, kaempherol, beta carotene, vitamin C, etc., which are known to have antioxidant, anti-carcinogenic, diuretic, nerve stabilizing, anti-constipation and immunity-enhancing effects, etc. With regard to its application to the skin, for example, Korean Patent No. 10-0756669 discloses the whitening activity of peach flesh. However, the application of a peach sprout extract to regulate the secretion of sebum has not yet been reported.

Peony is known to contain many types of sugars, mucilage, organic acids and trace minerals in a large amount and thus to treat malnutrition and to have an astringent function. Peony improves the vascular function, strengthens the digestive organs, and suppresses the pain in the nervous system. With regard to its application to the skin, for example, Korean Patent No. 10-0893912 discloses the effect of peony and *Gastrodia elata* extracts on the improvement of wrinkles and anti-aging, and Korean Patent No. 10-0286534 discloses an antioxidant tea comprising a peony extract. Also, Japanese Patent Laid-Open No. 2015-086183 discloses an anti-aging effect of a peony extract.

However, the prior art suggests nowhere the technical characteristic that a mixed extract of peony and peach sprout exhibits a significantly increased effect in the regulation of sebum secretion.

SUMMART OF INVENTION

Technical Problem

In one aspect, an object of the present invention is to provide a composition for inhibiting sebum secretion comprising a peach sprout extract as an active ingredient.

In another aspect, an object of the present invention is to provide a composition for inhibiting sebum secretion comprising a mixed extract of peach sprout and peony as an active ingredient.

Solution to Problem

In one aspect, the technique disclosed herein provides a composition for inhibiting sebum secretion comprising a peach sprout extract as an active ingredient.

In one exemplary embodiment, the active ingredient may further comprise a peony extract.

In one exemplary embodiment, the peony extract may be an extract of the roots and flowers of peony.

In one exemplary embodiment, the peony extract may be extracted using water as an extraction solvent.

In one exemplary embodiment, the peach sprout extract and the peony extract may be mixed at a weight ratio of 1:4 to 1:32.

In one exemplary embodiment, the composition may ameliorate diseases caused by excessive secretion of sebum.

In one exemplary embodiment, the diseases may be acne or seborrheic dermatitis.

In one exemplary embodiment, the active ingredient may reduce the level of neutral lipid production in sebum cells.

In one exemplary embodiment, the content of the active ingredient may be 0.01 to 50% by weight based on the total weight of the composition.

In one exemplary embodiment, the composition may be a cosmetic composition.

Advantageous Effects of Invention

In one aspect, the technique disclosed herein has the effect of providing a composition for inhibiting sebum secretion comprising a peach sprout extract as an active ingredient.

In one aspect, the technique disclosed herein has the effect of providing a composition for inhibiting sebum secretion comprising a mixed extract of peach sprout and peony as an active ingredient.

BEST MODE

Figure 1:
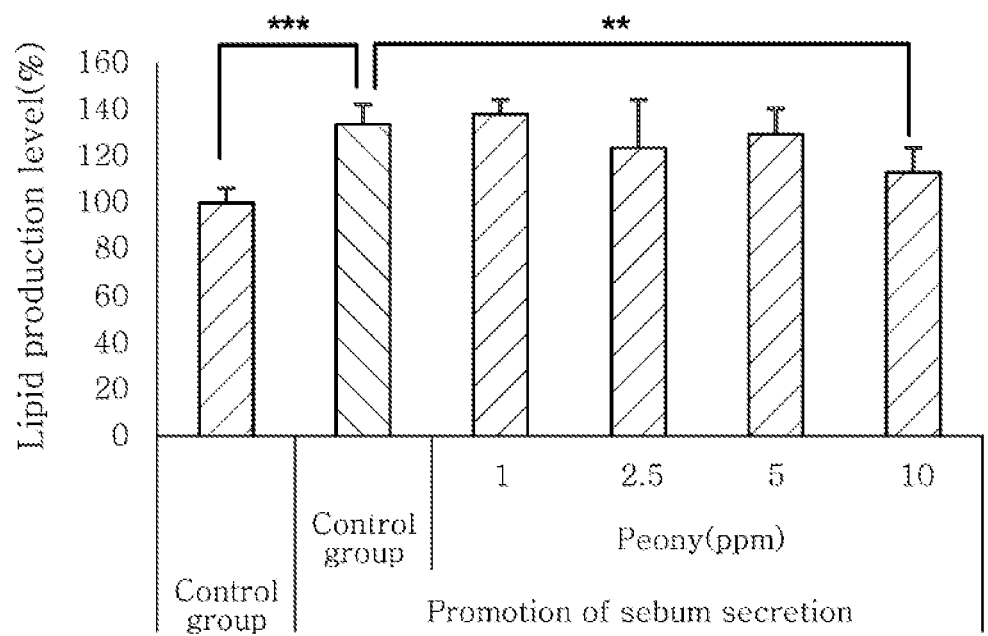
FIG. 1 shows the results of observation of the sebum control effect of a peony extract in a test example of the present invention (: $p<0.01$ versus Control, *: $p<0.001$ versus Control).
Figure 2A:
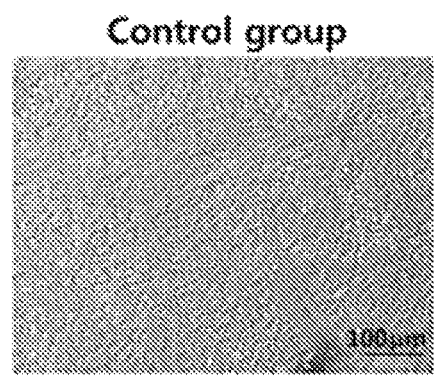
FIG. 2A to FIG. 2D show the results of observation of the sebum control effect of a peony extract in a test example of the present invention (: $p<0.01$ versus Control, *: $p<0.001$ versus Control).
Figure 2B:
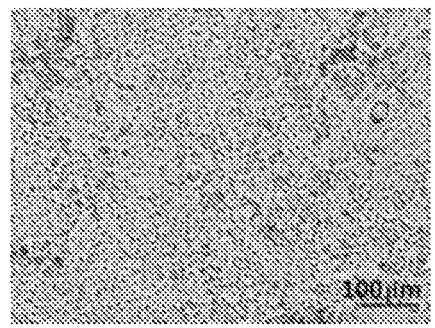
Figure 2C:
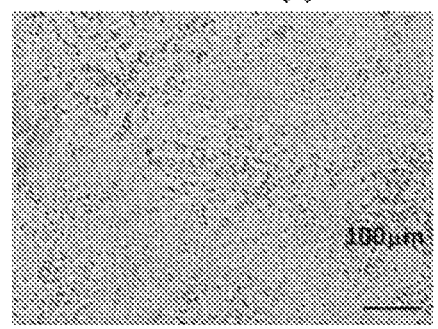
Figure 2D:
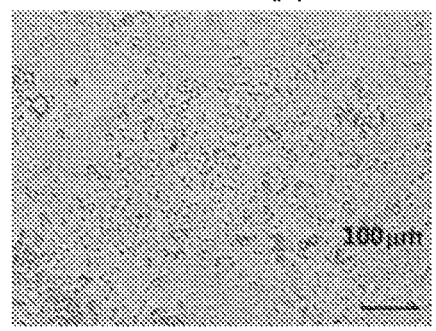
Figure 3:
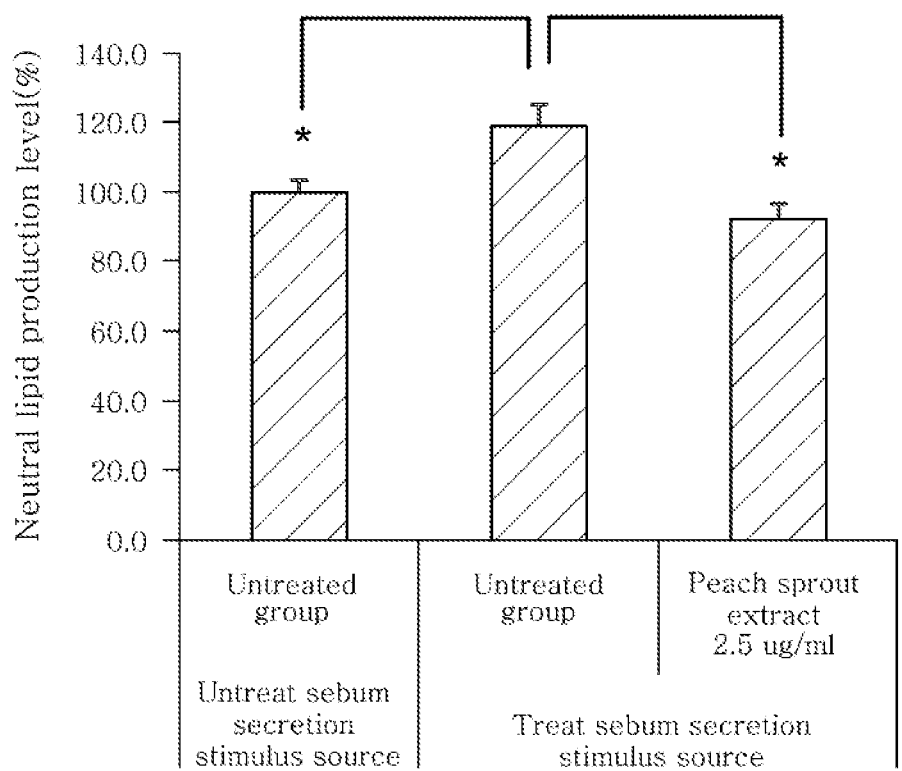
FIG. 3 shows the results of observation of the sebum control effect of a peach sprout extract in a test example of the present invention (*: $p<0.05$ versus Control).

Hereinafter, the present invention will be described in detail.

In one aspect, the technique disclosed herein shows that a peach sprout extract exerts an excellent effect in inhibiting sebum secretion.

In another aspect, the technique disclosed herein shows that a mixed extract of peach sprout and peony exhibits a synergistic effect in inhibiting sebum secretion.

Overproduction of sebum leads to denaturation and reduction of the collagen fibers and elastic fibers supporting the pore walls, thus reducing skin elasticity, which in turn results in aging and enlargement of the pores. The extract disclosed herein can inhibit the overproduction of sebum and regulate the secretion of sebum, thereby not only imparting elasticity to the pores but also suppressing the aging of the pores and exhibiting a pore-contraction effect.

As used herein, the term "active ingredient" refers to an ingredient that exhibits the desired activity by itself or an ingredient which can exhibit the desired activity together with a carrier which itself has no activity, etc.

The sprout refers to a state after germination and before the leaves are out, and the peach sprout extract refers to a material extracted from a young peach plant that has sprouted. The sprout can be considered as a stem cell of a plant. Unlike animals, plants have the potential for the entire plant body to become stem cells, because plants have only tissues and have not been differentiated into organs. Representative adult stem cells of plants are cells in the growing points of the ends of the roots or stems, and their seeds and the like correspond to the embryonic stem cells of animals. Sprouts are rich in various materials including vitamins, proteins, amino acids, minerals, etc. that are needed for growth.

Peony (*Paeonia lactiflora Pall.*) is a perennial herbaceous plant of the genus *Paeonia* in the family Paeoniaceae, which is a dicotyledon. It grows in mountainous areas. It has several stems, stands straight, and is about 60 cm tall. It has no hairs on the leaves and stems. It has several roots, which have a thick cylindrical shape with thin, pointed and long ends. The leaves are alternate, and the lower leaves are compound leaves with three small leaves coming out twice. A single flower blooms at the end of each stem in May to June. The flowers are large and beautiful and grow to about 10 cm in diameter. The flowers have various colors, including red and white. It has many horticultural varieties. The fruits are ovate with the end bent like a hook and are split along the ventral suture. The seeds are spherical. The flowers are beautiful and thus used for gardening. The roots are used as medicines for pain, stomach pain, menstrual pain, amenorrhea, hematemesis, anemia, bruise, etc.

As used herein, the extract encompasses not only crude extracts but also processed extracts in any form obtained by additional processing such as drying, concentration, fractionation, refinement, and fermentation.

In one exemplary embodiment, the peony extract may be obtained from the entire range of the plant without limitation, including the roots, stems, leaves and flowers. Preferably, the roots and flowers of peony can exert an excellent effect in inhibiting sebum secretion. Cultivated or commercially available peach sprout and peony may be used without limitation as the peach sprout and peony.

In one exemplary embodiment, the mixed extract may be a mixture obtained from the simultaneous extraction of peach sprout and peony or a mixed extract prepared by mixing each extract.

In one exemplary embodiment, the composition may comprise the peach sprout extract and the peony extract at a weight ratio of 1:4 to 1:32. For example, the composition may comprise the peach sprout extract and the peony extract at a weight ratio of 1:4 to 32, 1:4 to 30, 1:4 to 28, 1:4 to 26, 1:4 to 24, 1:4 to 22, 1:4 to 20, 1:4 to 18, 1:4 to 16, 1:4 to 14, 1:4 to 12, 1:4 to 10, 1:4 to 8, 1:4 to 6, or 1:4, thereby exhibiting an excellent sebum control effect. For example, it may be preferable in terms of sebum control effect that the composition comprises the peach sprout extract and the peony extract at a weight ratio of 1:4 to 5.

In one exemplary embodiment, the extract may be prepared according to a conventional extraction method used in the art.

For example, it may be extracted using a solvent extraction method using an extraction solvent selected from the group comprising water, an anhydrous or hydrated alcohol having 1 to 6 carbon atoms (e.g., methanol, ethanol, propanol, or butanol), propylene glycol, butylene glycol, dipropylene glycol, glycerin, acetone, ethyl acetate, chloroform, methylene chloride, butyl acetate, diethyl ether, dichloromethane, hexane, and mixtures thereof, preferably using water as an extraction solvent, a supercritical extraction method, an ultrasonic extraction method, or fermentation or natural fermentation metabolism using microorganisms. Alternatively, it may be extracted using a hot water extraction method, a cold extraction method, a reflux cooling extraction method or the like. The extraction solvent is not limited to the extraction solvents listed above. The specific amount of the extraction solvent used may be 5 to 100 times, 10 to 100 times, or 10 to 50 times the dry weight of the sample to be extracted, and the extraction time may be 1 to 24 hours or 2 to 10 hours.

In one exemplary embodiment, the content of the active ingredient may be 0.01 to 50% by weight based on the total weight of the composition. The content range of the active ingredient included in the composition allows to exhibit an excellent activity in inhibiting sebum secretion at an appropriate composition ratio of other ingredients and may be preferable in terms of economic feasibility and efficiency. Specifically, the content of the active ingredient may be 0.01 to 40% by weight, 0.01 to 30% by weight, 0.01 to 20% by weight, 0.01 to 15% by weight, 0.01 to 10% by weight, 0.05 to 10% by weight, 1.0 to 10% by weight, or 1.0 to 5% by weight based on the total weight of the composition.

In one exemplary embodiment, the composition may ameliorate diseases caused by excessive secretion of sebum.

In one exemplary embodiment, the diseases may be acne or seborrheic dermatitis.

In one exemplary embodiment, the active ingredient may reduce the level of neutral lipid production in sebum cells.

In one exemplary embodiment, the neutral lipid may be triacylglycerol.

In another aspect, the technique disclosed herein provides a method for inhibiting sebum secretion, comprising administering a mixed extract of peach sprout and peony to a subject in need thereof in an amount effective for inhibiting sebum secretion.

In another aspect, the technique disclosed herein provides a method for prevention, amelioration, and/or treatment of diseases associated with excessive secretion of sebum, such as acne or seborrheic dermatitis, comprising administering a mixed extract of peach sprout and peony to a subject in need thereof in an amount effective against diseases associated with excessive secretion of sebum, such as acne or seborrheic dermatitis.

In another aspect, the technique disclosed herein provides a mixed extract of peach sprout and peony for inhibiting sebum secretion in a subject.

In another aspect, the technique disclosed herein provides a mixed extract of peach sprout and peony for prevention, amelioration, and/or treatment of diseases associated with excessive secretion of sebum, such as acne or seborrheic dermatitis, in a subject.

In another aspect, the technique disclosed herein provides a use for preparation of a composition for inhibiting sebum secretion in a subject, containing a mixed extract of peach sprout and peony.

In another aspect, the technique disclosed herein provides a use for preparation of a composition for prevention, amelioration, and/or treatment of diseases associated with excessive secretion of sebum, such as acne or seborrheic dermatitis, in a subject, containing a mixed extract of peach sprout and peony.

In one exemplary embodiment, the extract may be applied or administered to a subject in the form of a pharmaceutical composition, a cosmetic composition, or a food composition.

In one exemplary embodiment, the extract may be applied or administered to the skin or scalp of a subject.

In one exemplary embodiment, the composition may be a pharmaceutical composition.

In one exemplary embodiment, the pharmaceutical composition may prevent or treat diseases caused by excessive secretion of sebum.

In addition to the extract, the pharmaceutical composition may further contain a pharmaceutical adjuvant such as a preservative, a stabilizer, a hydrating agent or an emulsifying accelerator, a salt and/or a buffer for controlling osmotic pressure, etc., and other therapeutically useful substances. It may be prepared into various formulations for oral or parenteral administration by a conventional method.

The formulation for oral administration may be, for example, a tablet, a pill, hard and soft capsules, a liquid, a suspension, an emulsion, a syrup, a dust, a powder, a fine granule, a granule, a pellet, etc. These formulations may comprise, in addition to the active ingredient, a surfactant, a diluent (e.g., lactose, dextrose, sucrose, mannitol, sorbitol, cellulose and glycine), and a lubricant (e.g., silica, talc, stearic acid and magnesium or calcium salt thereof, and polyethylene glycol). The tablet may comprise a binder such as magnesium aluminum silicate, starch paste, gelatin, tragacanth, methyl cellulose, sodium carboxymethyl cellulose and polyvinylpyrrolidone, and optionally a pharmaceutical additive such as a disintegrant, e.g. starch, agar, alginic acid or a sodium salt thereof, an absorbent, a colorant, a flavoring agent, a sweetener, etc. The tablet may be prepared according to a common mixing, granulation or coating method.

The formulation for parenteral administration may be a transdermal formulation, for example, injections, drops, ointments, lotions, gels, creams, sprays, suspensions, emulsions, suppositories, patches, etc., although not limited thereto.

The determination of the dose of the active ingredient is within the knowledge of those skilled in the art. The daily dose of the drug will vary depending on various factors such as the progress and the time of onset of the disease, the age, and the health condition of the subject, complications, etc. However, in one aspect, the dose for adults may be 1 µg/kg to 200 mg/kg of the composition in one to three divided doses per day. In another aspect, it may be 50 µg/kg to 50 mg/kg of the composition in one to three divided doses per day. The dose does not limit the scope of the present invention by any means.

The pharmaceutical composition may be an agent for external application to the skin. The agent for external application to the skin is a generic term that refers to any substance applied to the skin exterior and encompasses medicines of various formulations.

In one exemplary embodiment, the composition may be a cosmetic composition.

The cosmetic composition may further comprise, in addition to the extract, a functional additive and ingredients that are generally used in cosmetic compositions. The functional additive may include an ingredient selected from the group consisting of water-soluble vitamins, oil-soluble vitamins, polypeptides, polysaccharides, sphingolipids, and seaweed extracts. Examples of other additional ingredients include oil and fat ingredients, moisturizers, emollients, surfactants, organic and inorganic pigments, organic powders, UV absorbers, preservatives, sterilizers, antioxidants, plant extracts, pH adjusters, alcohols, colorants, fragrances, blood circulation stimulants, skin coolers, deodorants, purified water, etc.

The formulation of the cosmetic composition is not specifically limited, and may be suitably selected depending on the intended use. For example, it may be formulated into one or more formulations selected from the group consisting of a skin lotion, a skin softener, a skin toner, an astringent, a lotion, a milk lotion, a moisture lotion, a nourishing lotion, a massage cream, a nourishing cream, a moisture cream, a hand cream, a foundation, an essence, a nourishing essence, a pack, a soap, a cleansing foam, a cleansing lotion, a cleansing cream, a body lotion, and a body cleanser, although not limited thereto.

When the formulation of the present invention is a paste, a cream, or a gel, an animal oil, a vegetable oil, wax, paraffin, starch, tragacanth, cellulose derivatives, polyethylene glycol, silicone, bentonite, silica, talc, zinc oxide or the like may be used as a carrier ingredient.

When the formulation of the present invention is a powder or a spray, lactose, talc, silica, aluminum hydroxide, calcium silicate or polyamide powder may be used as a carrier ingredient. In particular, when the formulation is a spray, it may further comprise a propellent such as chlorofluorohydrocarbon, propane/butane or dimethyl ether.

When the formulation of the present invention is a solution or an emulsion, a solvent, a solubilizer, or an emulsifier may be used as a carrier ingredient. Examples of this carrier ingredient include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan.

When the formulation of the present invention is a suspension, it may contain, as a carrier ingredient, a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, or tragacanth, etc.

When the formulation of the present invention is a surfactant-containing cleanser, it may contain, as a carrier ingredient, aliphatic alcohol sulfate, aliphatic alcohol ether sulfate, sulfosuccinic monoester, isethionate, imidazolinium derivatives, methyl taurate, sarcosinate, fatty acid amide ether sulfate, alkyl amidobetaine, aliphatic alcohol, fatty acid glyceride, fatty acid diethanolamide, vegetable oil, lanoline derivatives, or ethoxylated glycerol fatty acid ester.

In one exemplary embodiment, the composition may be a food composition.

The food composition may be in a liquid or solid formulation. For example, it may be various foods, beverages, gums, tea, vitamin complexes, health supplements, etc. It may be in the form of a powder, a granule, a tablet, a capsule or a beverage. The food composition in the form of each formulation may further comprise an ingredient commonly used in the pertinent field in addition to the active ingredient. The ingredient may be selected and added without difficulty by those skilled in the art according to the desired formulation or purpose. The addition of other ingredient may give a synergic effect.

There are no particular limitations on the liquid ingredients that may be contained in addition to the active ingredient disclosed herein. It may comprise various flavoring agents or natural carbohydrates as additional ingredients, as do common beverages. Examples of natural carbohydrates are conventional sugars such as monosaccharide, disaccharides such as glucose and fructose, polysaccharides such as maltose and sucrose, dextrin, cyclodextrin, etc. and sugar alcohols such as xylitol, sorbitol, erythritol, etc. Also, natural flavoring agents (thaumatin, stevia extract (e.g., rebaudioside A, glycyrrhizin, etc.)) and synthetic flavoring agents (e.g., saccharin, aspartame, etc.) may be advantageously used as the flavoring agent. In general, the content of the natural carbohydrate may be about 1 to 20 g, and in one aspect, about 5 to 12 g per 100 ml of the composition disclosed herein.

In one aspect, the food composition may comprise various nutrients, a vitamin, a mineral (electrolyte), flavoring agents such as a synthetic flavoring agent and a natural flavoring agent, a colorant and an improving agent (cheese, chocolate, etc.), pectic acid or a salt thereof, alginic acid or a salt thereof, an organic acid, a protective colloidal thickening agent, a pH adjuster, a stabilizer, a preservative, glycerin, alcohol, a carbonating agent as used in carbonated beverages, etc. In another aspect, it may comprise fruit flesh for the production of natural fruit juices and vegetable beverages. These ingredients may be used alone or as a mixture thereof. The amount of the additive may vary. However, generally it is 0.001 to about 20 parts by weight with respect to 100 parts by weight of the composition disclosed herein.

[Modes for Invention]

Hereinafter, the present invention will be described in further detail with reference to examples. It will be apparent to those skilled in the art that these examples are for illustrative purposes only and are not intended to limit the scope of the present invention.

Example 1

Preparation of Extracts (1) A Peony Extract

Peony (*Paeonia albiflora*) roots were subjected to heat treatment at 80° C. for 1 hour. Then, the peony roots and peony flowers were crushed. The crushed peony roots and flowers were extracted with distilled water overnight at room temperature. The resultant was centrifuged, filtered through a 1 μm filter, and complexed with propanediol, followed by filtration through a 0.45 μm filter to obtain a peony extract.

(2) A Peach Sprout Extract

A peach sprout extract was obtained from GREENTECH (http://www.greentech.fr/en/).

(3) A mixed extract of peach sprout and peony

The prepared peony extract and peach sprout extract were mixed at various ratios to prepare mixed extracts.

Test Example 1

Sebum Control Effect

Cells were stained using the Oil Red O staining method to stain the neutral lipids (triacylglycerol, cholesterol ester) in the cells. The sebum control effect of each extract was compared by comparing the images or comparing the absorbances after dissolution in isopropanol.

Specifically, primary sebocytes were seeded in a 24-well plate at a concentration of $6 \times 10^4$ cells/well and cultured overnight. In order to promote sebum secretion, 50 μM linoleic acid, 50 μM arachidonic acid, and 50 nM dihydrotestosterone were applied as stimuli. The cells were treated or not treated with each of the extracts prepared in Example 1, and then cultured for 4 days. The medium was then removed, followed by washing with PBS. Then, 10% paraformaldehyde in PBS was added and the cells were fixed for 15 minutes. The cells were then washed again with PBS. Then, the cells were treated with Oil Red O staining solution for 15 minutes and then washed with EtOH and DIW to remove excess dye. The cells were then placed in PBS and observed under a microscope. PBS was then removed and 4% NP-40 in isopropyl alcohol was added to the cells to dissolve the dye in the cells. The absorbance was measured at 520 nm. The degree of production of neutral lipid was calculated as a percentage relative to the non-stimulated group (the group not treated with the extracts) and compared to evaluate sebum control effect.

From the results, it was found that, despite the promotion of sebum secretion, the peony extract reduced neutral lipid production level, while the induction control group, which is a positive control group, showed an increase in neutral lipid production level. Thus, it was confirmed that the peony extract has the effect of inhibiting sebum (see FIG. 1). This was also visually confirmed by microscopic observation (see FIG. 2A to FIG. 2D).

Figure 4:
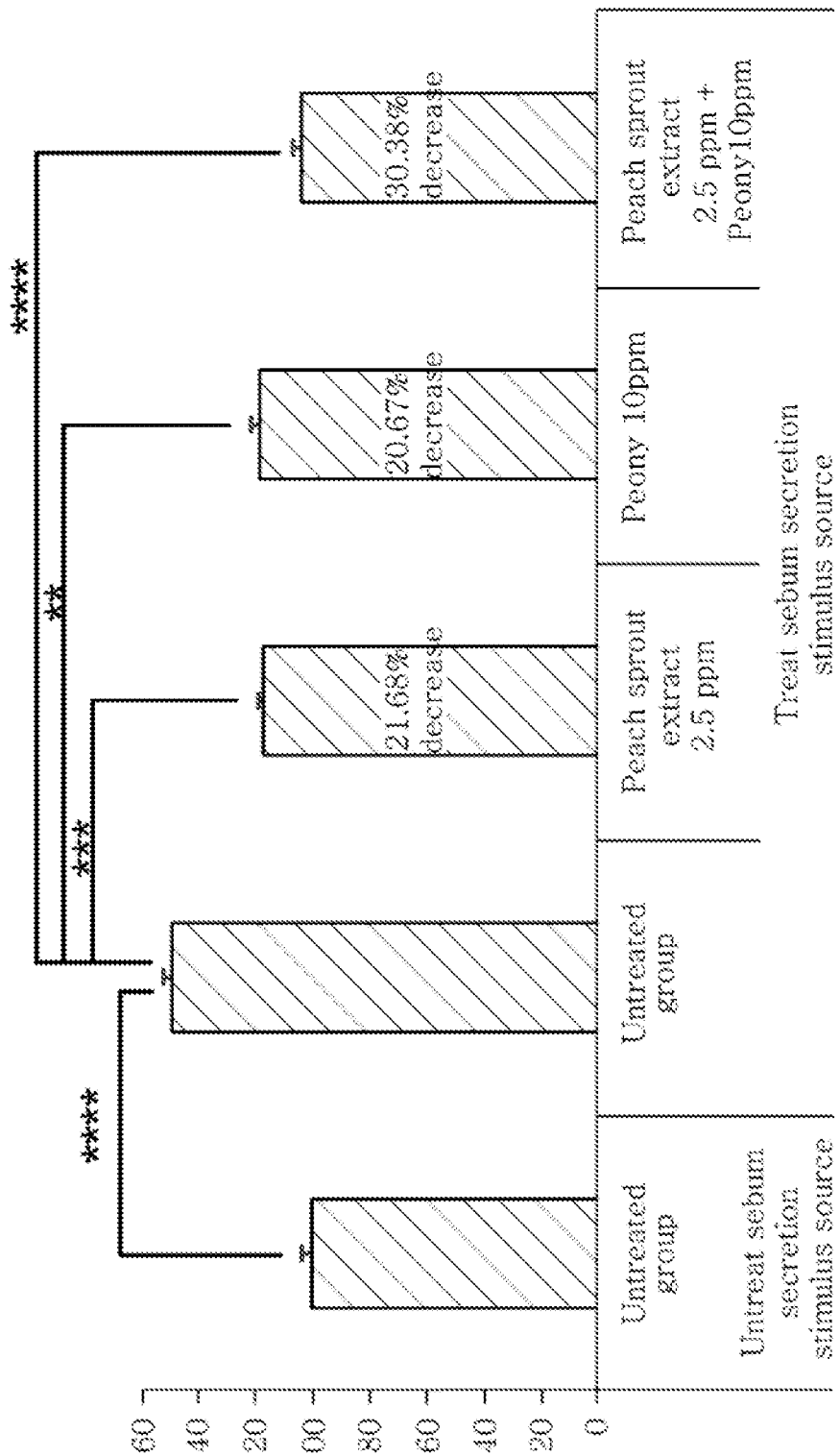
FIG. 4 shows the results of observation of the sebum control effect of a mixed extract of peach sprout and peony in a test example of the present invention (: $p<0.01$ versus Control, *: $p<0.001$ versus Control, ****: $p<0.0001$ versus Control).

In addition, it was found that the mixed extract of peach sprout and peony showed a neutral lipid production level close to that of the non-treated group, while the stimulated non-treated group, which is a positive control group, showed a very high neutral lipid production level, which shows that the mixed extract exhibits a sebum production level similar to that of the non-treated group, despite the promotion of sebum secretion (See FIG. 4). Further, the sebum inhibitory effect of the mixed extract of peach sprout and peony was found to be remarkably superior to that of each of the peony extract and the peach sprout extract, indicating that the mixed extract of peach sprout and peony significantly reduces neutral lipid production level and thus has a synergistic effect in inhibiting sebum.

Hereinafter, formulation examples of the composition according to one aspect of the present invention will be described. However, it may be formulated into various other forms. These examples are for illustrative purposes only and are not intended to limit the scope of the present invention.

Formulation Example 1

Preparation of Soaps

Mixed extract of peach sprout and peony: 1.00(%)
Oil and fat: q.s.
Sodium hydroxide: q.s.

Sodium chloride: q.s.
Fragrance: small amount
The total amount was adjusted to 100 with purified water.
A soap was prepared according to the above composition ratio (%).

Formulation Example 2

Preparation of Lotions

Mixed extract of peach sprout and peony: 3.00(%)
L-ascorbic acid-2-phosphate magnesium salt: 1.00
Water-soluble collagen (1% aqueous solution): 1.00
Sodium citrate: 0.10
Citric acid: 0.05
Licorice root extract: 0.20
1,3-butylene glycol: 3.00
The total amount was adjusted to 100 with purified water.
A lotion was prepared according to the above composition ratio (%)

Formulation Example 3

Preparation of Creams

Mixed extract of peach sprout and peony: 1.00(%)
Polyethyleneglycol monostearate: 2.00
Self-emulsifying glycerin monostearate: 5.00
Cetyl alcohol: 4.00
Squalene: 6.00
Glyceryl tri-2-ethylhexanoate: 6.00
Sphingoglycolipid: 1.00
1,3-butylene glycol: 7.00
The total amount was adjusted to 100 with purified water.
A cream was prepared according to the above composition ratio (%)

Formulation Example 4

Preparation of Packs

Mixed extract of peach sprout and peony: 5.00(%)
Polyvinyl alcohol: 13.00
L-ascorbic acid-2-phosphate magnesium salt: 1.00
Lauroyl hydroxyproline: 1.00
Water-soluble collagen (1% aqueous solution): 2.00
1,3-butylen glycol: 3.00
Ethanol: 5.00
The total amount was adjusted to 100 with purified water.
A pack was prepared according to the above composition ratio (%).

Formulation Example 5

Preparation of Cosmetic Solutions

Mixed extract of peach sprout and peony: 2.00(%)
Hydroxyethylene cellulose (2% aqueous solution): 12.00
Xanthan gum (2% aqueous solution): 2.00
1,3-butylene glycol: 6.00
Concentrated glycerin: 4.00
Sodium hyaluronate (1% aqueous solution): 5.00
The total amount was adjusted to 100 with purified water.
A cosmetic solution was prepared according to the above composition ratio (%).

Formulation Example 6

Preparation of Powders

Mixed extract of peach sprout and peony: 300 mg
Lactose: 100 mg
Talc: 10 mg
The above ingredients were mixed and filled in an airtight pouch to prepare a powder.

Formulation Example 7

Preparation of Tablets

Mixed extract of peach sprout and peony: 50 mg
Corn starch: 100 mg
Lactose: 100 mg
Magnesium stearate: 2 mg
The above ingredients were mixed and tabletted according to a conventional method for preparing tablets, to prepare a tablet.

Forulation Example 8

Preparation of Capsules

Mixed extract of peach sprout and peony: 50 mg
Corn starch: 100 mg
Lactose: 100 mg
Magnesium stearate: 2 mg
The above ingredients were mixed and filled in a gelatin capsule according to a conventional method for preparing capsules to prepare a capsule.

Formulation Example 9

Preparation of Injections

Mixed extract of peach sprout and peony: 50 mg
Sterilized distilled water for injection: q.s.
pH adjuster: q.s.
An injection was prepared according to a conventional method for preparing injections using the above amounts of ingredients per ampoule (2 ml).

Formulation Example 10

Preparation of Liquid Preparations

Mixed extract of peach sprout and peony: 100 mg
Isomerized sugar: 10 g
Mannitol: 5 g
Purified water: q.s.
According to a conventional method for preparing liquid preparations, the above ingredients were added and dissolved in purified water. After adding an adequate amount of lemon flavoring, the ingredients were mixed. Then, purified water was added to make 100 ml. The prepared liquid preparation was filled in a brown bottle and sterilized to prepare a liquid preparation.

While the present invention has been described with respect to the specific embodiments, it will be apparent to those skilled in the art that the above descriptions are only preferred embodiments and that the scope of the present invention is not limited thereto. Thus, the scope of the present invention should be defined by the appended claims and equivalents thereof.

The invention claimed is:

1. A method for reducing sebum secretion comprising administering an effective amount of a peach sprout extract and a peony extract for reducing sebum secretion to a subject in need thereof wherein the peach sprout extract and the peony extract are mixed at a weight ratio of 1:4 to 1:32.

2. The method according to claim 1,
wherein the peony extract is an extract of the roots and flowers of peony.

3. The method according to claim 1,
wherein the peony extract is obtained using water as an extraction solvent.

4. The method according to claim 1,
wherein the peach sprout extract and the peony extract ameliorate diseases caused by excessive secretion of sebum.

5. The method according to claim 4,
wherein the diseases are acne or seborrheic dermatitis.

6. The method according to claim 1,
wherein the peach sprout extract and a peony extract reduces the level of neutral lipid production in sebum cells.

7. The method according to claim 1,
wherein the peach sprout extract and a peony extract are administered to the subject in a form of a composition, and the composition comprises 0.01 to 50% by weight of the peach sprout extract and a peony extract based on the total weight of the composition.

8. The method according to claim 1,
wherein the peach sprout extract and a peony extract are administered to the subject in a form of a composition, and the composition is a cosmetic composition.

9. The method according to claim 1,
wherein the peach sprout extract is obtained using water as an extraction solvent.

* * * * *